United States Patent [19]

Nakata et al.

[11] Patent Number: 5,062,715
[45] Date of Patent: Nov. 5, 1991

[54] METHOD AND APPARATUS FOR DETECTING PHOTOACOUSTIC SIGNAL AND METHOD FOR DETECTING INTERNAL DEFECT OF SEMICONDUCTOR DEVICE

[75] Inventors: Toshihiko Nakata; Yukio Kembo, both of Yokohama, Japan

[73] Assignee: Hitachi, Ltd., Tokyo, Japan

[21] Appl. No.: 479,712

[22] Filed: Feb. 14, 1990

[30] Foreign Application Priority Data

Mar. 17, 1989 [JP] Japan .................................. 1-063604

[51] Int. Cl.$^5$ ...................... G01N 21/25; G01N 21/71
[52] U.S. Cl. .................................................... 356/432
[58] Field of Search ................... 356/432, 432 T, 444, 356/445; 310/311

[56] References Cited

U.S. PATENT DOCUMENTS 4,689,491 8/1987 Lindow et al. .................... 356/445
4,854,710 8/1989 Opsal et al. ........................ 356/432

OTHER PUBLICATIONS

M. Hangyo et al., "Photoacoustic Microscope", Hihakai Kensa, vol. 36, No. 10, Oct. 1987 (Showa 62), pp. 730–736.
P. Cielo et al., "Laser Generation of Convergent Acoustic Waves and Applications to Materials Evaluation", IEEE 1986 Ultrasonics Symposium, pp. 515–526.

*Primary Examiner*—Vincent P. McGraw
*Assistant Examiner*—LaCharles P. Keesee
*Attorney, Agent, or Firm*—Fay, Sharpe, Beall, Fagan, Minnich & McKee

[57] ABSTRACT

A photoacoustic signal detecting method and apparatus for intensity-modulating light having a wavelength penetrating a sample such as a semiconductor device at a desired frequency, the light being emitted from a first light source, focusing the intensity-modulated light on the sample as a light spot, by changing the position of the sample and the optical constant of the means for focusing, scanning the light spot inside the sample in a depth direction thereof to detect the photoacoustic effect generated in the sample, and extracting information relative to the surface and inside of the sample and defect information therein. The photoacoustic effect is detected using an interferometer. Light incident on the sample surface for a second light source in order to obtain interference light and the interference light reflected from the sample surface are adjusted in response to a signal indicative of the depth of the light spot to detect optimum interference light. Light reflected from the sample surface when light emitted from a third light source is incident on the surface is detected through the focusing optical system to generate the signal indicative of the depth of the light spot.

19 Claims, 18 Drawing Sheets

FIG. IA
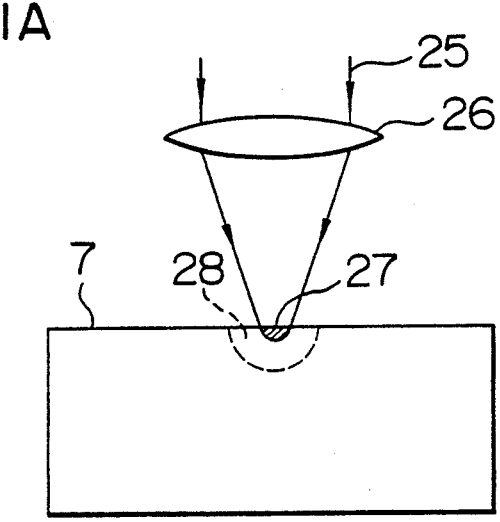
FIG. IB
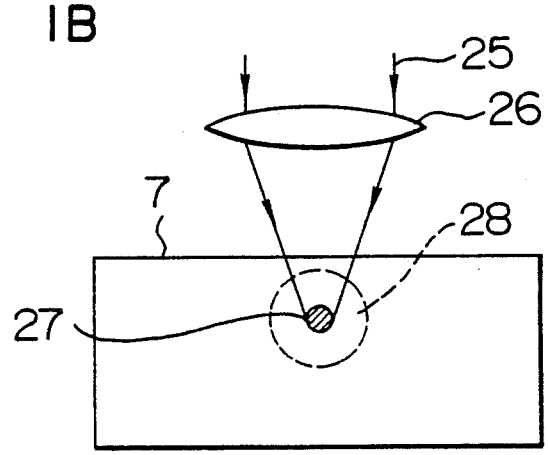
FIG. IC
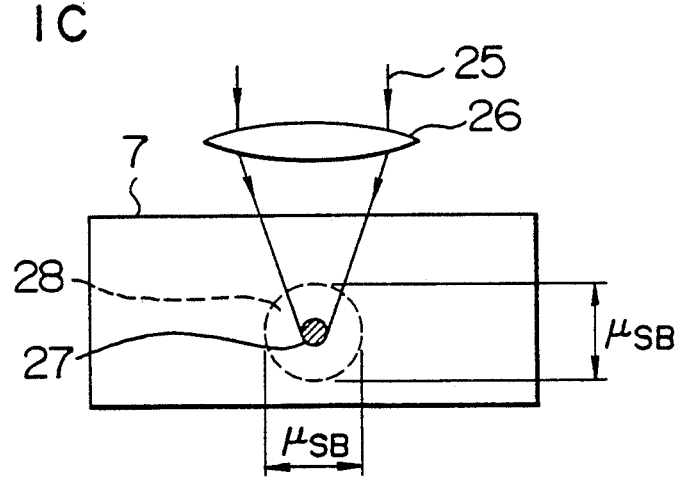

F I G. 3
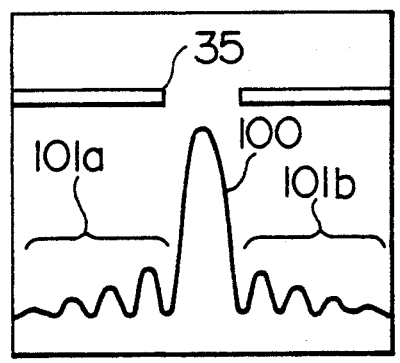
F I G. 4
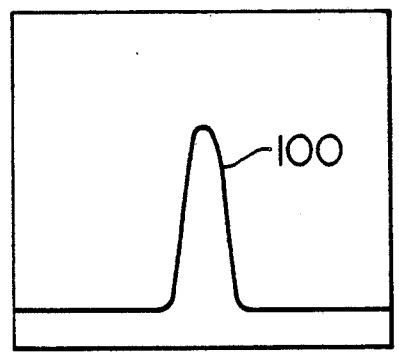

F I G. 12
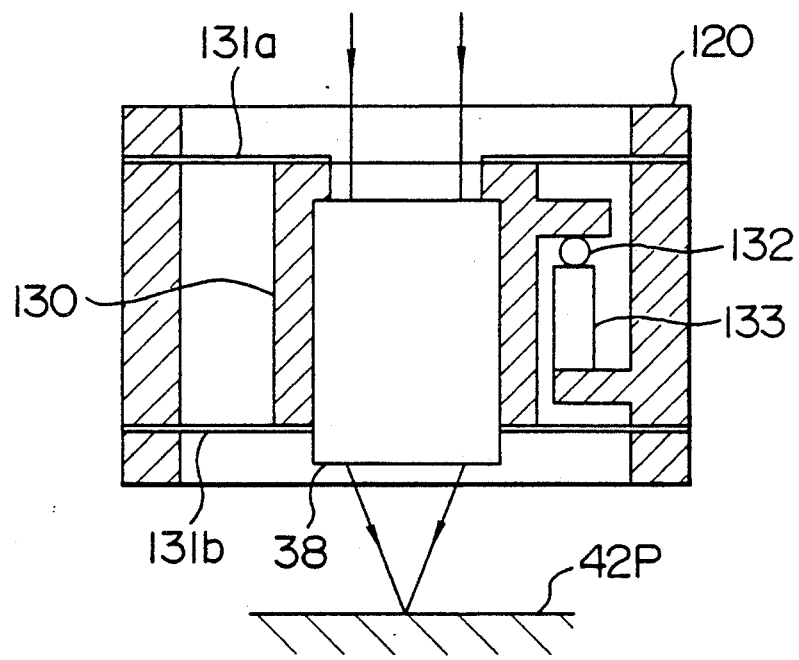

F I G. 21A
F I G. 21B
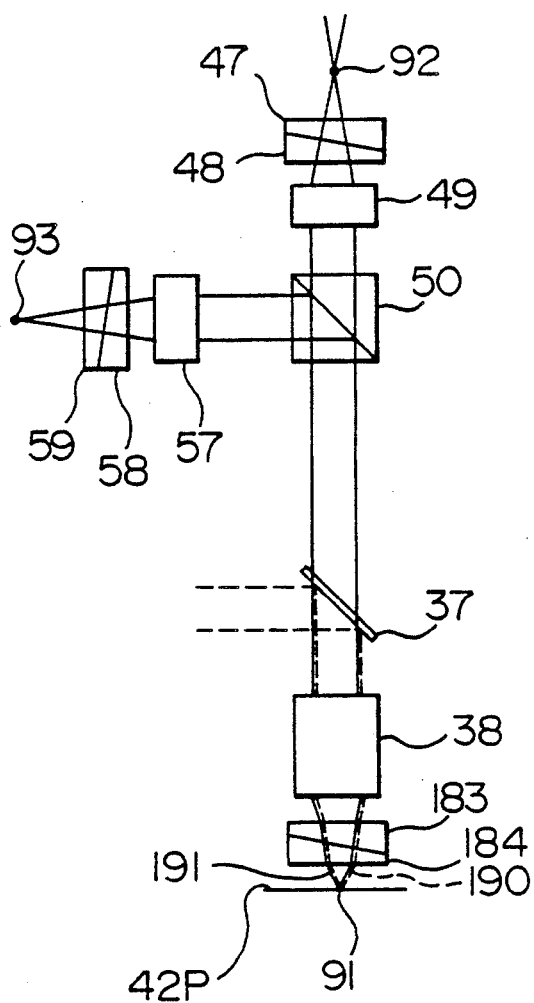
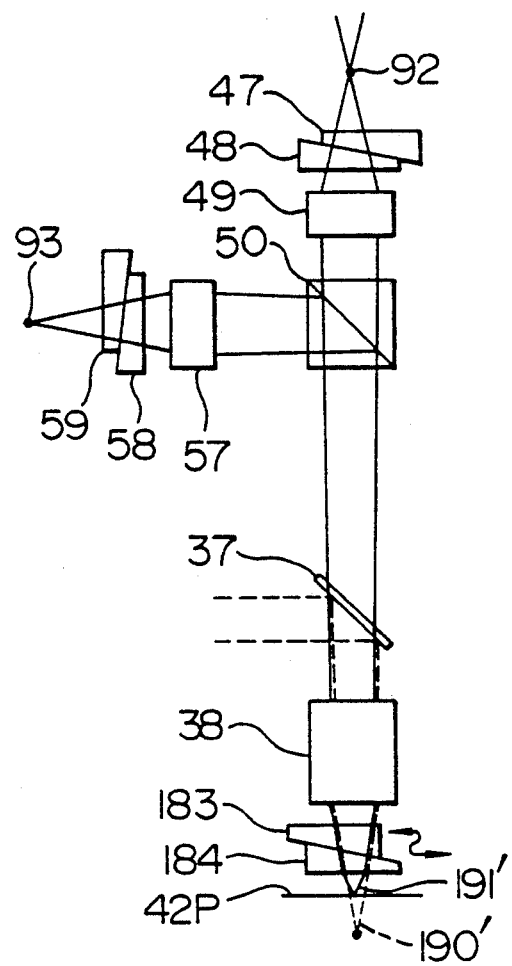

F I G. 24A
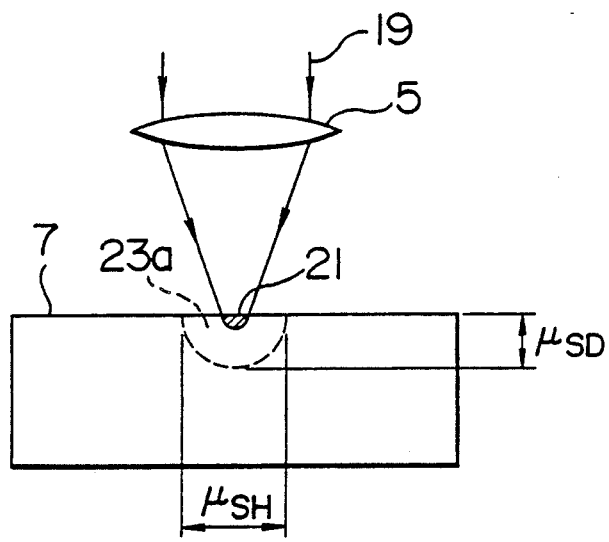
F I G. 24B
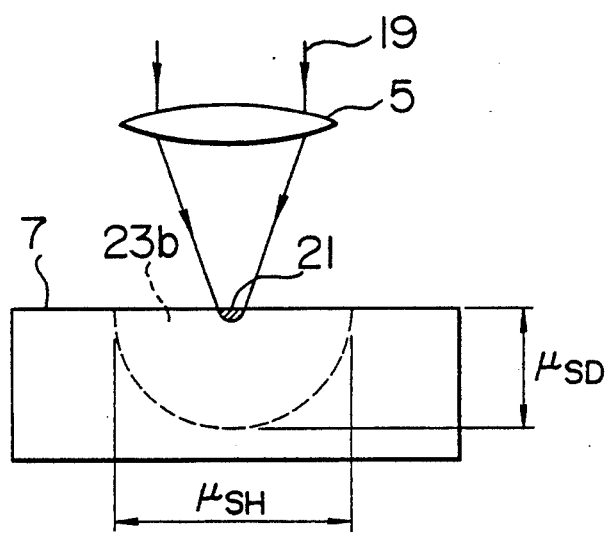

METHOD AND APPARATUS FOR DETECTING PHOTOACOUSTIC SIGNAL AND METHOD FOR DETECTING INTERNAL DEFECT OF SEMICONDUCTOR DEVICE

BACKGROUND OF THE INVENTION

The present invention relates to a photoacoustic signal detecting method and apparatus for detecting information relative to the surface and inside of a sample using photoacoustic effect, and a method for detecting internal defects of a semiconductor device.

The photoacoustic effect, which was discovered by Tyndall, Bell, Röntgen, et al. in 1881, represents the following phenomenon. When, as shown in FIG. 23, intensity-modulated light (intermittent light) 19 is irradiated to a sample 7, through a lens 5, heat is generated in a light absorption region Vop 21 and periodically diffused through a heat diffusion region Vth 23 defined by thermal diffusion length $\mu s$ so that the thermal distortion wave thus generated provides a surface acoustic wave (ultrasonic wave). By detecting this ultrasonic wave i.e. a photoacoustic wave by a microphone (acoustic-electric converter) or a piezo-electric element to obtain the component in synchronism with the incident light, information relative to the surface and inside of the sample can be obtained. A technique for detecting the above photoacoustic signal is disclosed in "HIHAKAI KENSA", Vol. 36, No. 10, pp. 730–736, October 1987 (Showa 62) or IEEE; 1986 ULTRASONIC SYMPOSIUM—pp. 515-526 (1986). Now referring to FIG. 22, this one example of technique will be explained in the case where a laser is used as a light source.

A parallel light emitted from a laser 1 is intensity-modulated by an acoustic-optical modulator element (AO converter) 2. The thus obtained intermittent light is expanded to a beam of a desired diameter by a beam expander 3, which is reflected by a beam splitter or half mirror 4 and thereafter focused on the surface of a sample 7 placed on an XY stage 6 by a lens 5. Then, the heat distortion wave created at a focusing position 21 generates an ultrasonic wave and also provides a minute displacement in the sample surface. This minute displacement will be detected by a Michelson interferometer explained below. A parallel light emitted from a laser 8 is expanded to a beam of a desired diameter by a beam expander 9. This beam is separated into two optical paths by a beam splitter or half mirror 10. The one is focused on the focusing position 21 on the sample 7 by a lens 5 whereas the other is irradiated to a reference mirror 11. Then, the light reflected from the sample 7 and the light reflected from the reference mirror 11 interfere with each other on the beam splitter 10. The interference pattern thus formed is focused on a photoelectric converting element 13 (e.g. photodiode) through a lens 12 to provide a photoelectric-converted interference intensity signal. This interference intensity signal is amplified by a preamplifier 14 and thereafter sent to a lock-in amplifier 16. The lock-in amplifier 16, using as a reference signal a modulated frequency signal from an oscillator 15 used for driving the acoustic-optical modulation element 2, extracts only the modulated frequency component contained in the interference intensity signal. This frequency component has information relative to the surface or inside of the sample according to the frequency. By varying the modulated frequency, the thermal diffusion length $\mu s$ 21, the information in a direction of the depth of the sample can be obtained (FIG. 23).

The inventors of the present invention, by improving the photoacoustic signal detecting apparatus as described above, disclosed the device with enhanced precision of detecting the information relative to the surface and inside of a sample in USSN 384541 filed July 24, 1989 entitled "Photoacoustic Signal Detecting Device" and assigned to the same assignee as the present application. In accordance with one aspect of the invention of this prior application, both focusing means for intensity-modulating the light emitted from a first laser light source to be focused on a sample, and interferometry detection means for detecting photoacoustic effect through interferometry and constructed in a confocal optical system so that the transverse resolution and detecting sensitivity of a photoacoustic signal can be improved, and hence the resultant device can be applied to e.g. a semiconductor device having a rugged surface.

The above mentioned technique is very efficient in that it enables a photoacoustic signal to be detected in a non-contact and non-destruction manner, but also has the following problem. Therefore, if there is a defect such as a crack inside thermal diffusion region Vth 23, the modulated frequency component in the interference intensity signal provides a signal change so that the presence of the defect can be noticed. Thus as shown in FIG. 23 an XY stage shifting signal and an output signal from the lock-in amplifier 16 are processed by a computer 17. Accordingly, the photoacoustic signals corresponding to the respective positions on the sample are displayed on a display (e.g. a monitor television) 18 as image information.

The resolution of a photoacoustic signal in both transverse and depth directions, if the light absorption region Vop 21, i.e. the spot diameter of laser light is smaller than the thermal diffusion region Vth 23, is defined as the thermal diffusion length $\mu s$ 23. This $\mu s$ can be defined by Equation (1)

$$\mu s = \sqrt{2k/\rho cf} \qquad (1)$$

where
k: thermal conductivity of a sample
$\rho$: density
c: specific heat
f: intensity-modulation frequency of a laser For example, when f=10 kHz, Si or Al has a $\mu s$ of $\sim 50$ $\mu m$, and SiO$_2$ has a $\mu s$ of $\sim 5$ $\mu m$.

Now if the thermal diffusion length 23a as shown in FIG. 24A is formed at a certain modulation frequency, the resolutions in the depth direction and the transverse (horizontal) direction are given as $\mu SD \approx \mu s$, and $\mu SH \approx 2 \mu s$, respectively. In order to obtain inside information at a deeper position, as understood from Equation (1), the modulation frequency f must be decreased to increase the thermal diffusion length $\mu s$ as shown in FIG. 24B. As a result, however, the transverse direction resolution $\mu SH$ and the depth direction resolution $\mu SD$ will be reduced. Specifically, if in the prior art, in order to obtain the information in the depth direction, the laser modulation frequency f is varied thereby to vary the thermal diffusion length $\mu s$, the resolutions in the transverse and depth directions will be disadvantageously varied. Particularly, in order to obtain the information at a deeper position, the thermal diffusion length μs must be further increased to reduce the resolutions. Thus, under the present conditions, it is very difficult to detect information inside of a sample with a miniaturized structure in the order of magnitude of μm.

SUMMARY OF THE INVENTION

An object of the present invention is to provide a method and apparatus for detecting a photoacoustic signal which can stably detect the inside information of a sample in a depth direction without reducing the resolutions in transverse and depth directions.

Another object of the present invention is to provide a method for detecting a defect in a semiconductor device by detecting the inside information of the semiconductor device in a depth direction.

In accordance with one aspect of the present invention, in an apparatus for detecting a photoacoustic signal comprising a first light source, modulation means for intensity-modulating the light emitted from the light source at a desired frequency, focusing means for the intensity-modulated light on a sample (e.g. semiconductor device) detecting means for detecting the photoacoustic effect generated in the sample, and information extraction means for the information relative to the surface and inside of the sample from the detected photoacoustic effect, by setting the wavelength of the light emitted from the first light source for that permitting the light to penetrate the sample and by scanning the focused light spot along the depth direction inside the sample, the inside information of the sample at any depth thereof can be stably detected without reducing the resolutions of the photoacoustic signal in transverse and depth directions of the sample.

In order to attain the above object of the present invention, there are provided interferometry detecting means for detecting the photoacoustic effect using interferometry, and focusing position controlling means so that in order to obtain the interferometry in the light interference detecting means, the light from a second light source incident on a sample surface is always focused on the sample surface as a light spot with a minimum size and the light reflected from the sample surface is focused on a photoelectric converting device as a light spot with a minimum size, whereby a photoacoustic signal can be stably detected.

In accordance with the present invention, by using, as excited light for generating a heat distortion wave and ultrasonic wave, the light with a wavelength able to penetrate the sample, and scanning the focused light spot in a depth direction of the sample without varying the modulation frequency, the inside information (e.g. internal defects of a semiconductor device) of the sample at any depth position can be stably detected without reducing the resolutions of a photoacoustic signal in the transverse and depth directions. Also, by constructing all the optical systems in confocal optical systems, the transverse resolution and detecting sensitivity of the photoacoustic signal can be improved, and also influence from multi-interference in a multi-layer film can be reduced which enables the present invention to be used to detect defects in e.g. a semiconductor device with a rugged surface. Moreover, by controlling the laser focused spot in the interference optical system so that it is always focused on the sample surface and the photoelectric converter, the photoacoustic signal can be stably detected. Further, disconnection, cracks, etc. in an integrated circuit and semiconductor device having a multi-layer structure can be detected.

BRIEF DESCRIPTION OF THE DRAWINGS

FIGS. 1A to 1C are sectional views showing the basic principle of the present invention;

FIG. 3 is a view for explaining the manner of shading the high order diffraction light component of a laser spot through a pin-hole;

FIG. 4 is a graph showing the light intensity distribution of a laser beam immediately after it has passed the pin-hole;

FIG. 12 is a sectional view showing the mechanism for minutely shifting an objective lens;

FIGS. 21A and 21B are views for explaining the method for controlling the focusing point of a laser beam;

FIGS. 24A and 24B are views for explaining the change in a thermal diffusion region due to the change in a modulation frequency.

DESCRIPTION OF THE PREFERRED EMBODIMENTS

Prior to explaining embodiments of the present invention, the basic theory thereof will be explained with reference to FIGS. 1A to 1C. In the present invention, as excited light for generating a heat distortion wave and ultrasonic wave in a sample (e.g. semiconductor device), the light having a waveform able to penetrate the sample is used. Next, the modulation frequency of the excited light is set to provide a thermal diffusion length exhibiting a desired resolution. In operation, as shown in FIGS. 1A to 1C, the focusing spot (light absorbing area) position 27 of the excited light is canned in a depth direction of the sample without varying the modulation frequency. In accordance with the above basic theory, unlike the prior art, the inside information of the sample at any depth position can be stably obtained without reducing the resolutions in both transverse and depth directions. In this case, resolutions are fixed to $\mu_{SB}$ in both directions on the sample surface and at sample inner portion, respectively.

Figure 2:
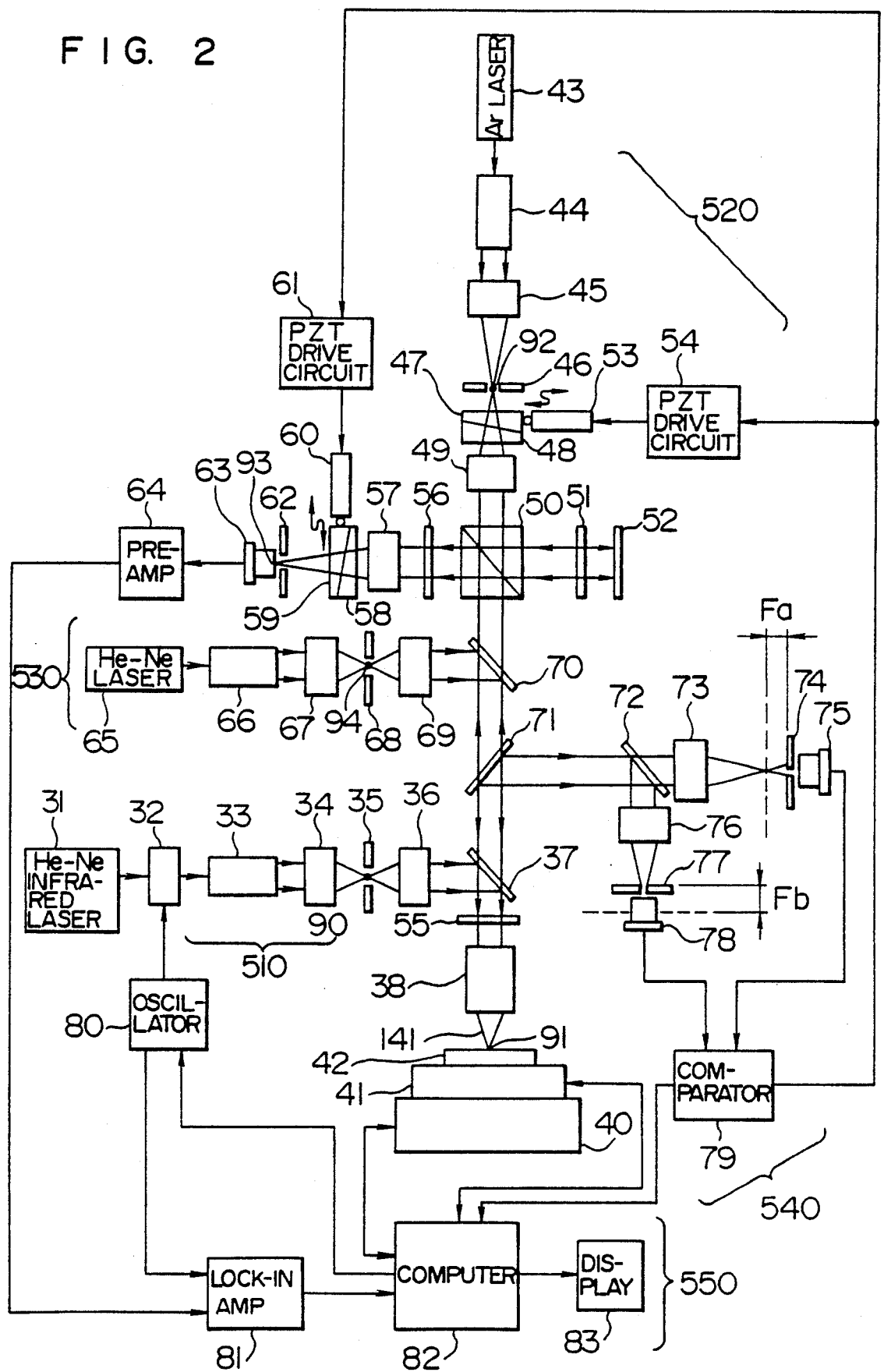
FIG. 2 is a block diagram of the photoacoustic signal detecting optical system in accordance with a first embodiment of the present invention.

First, a first embodiment of the present invention will be explained with reference to FIGS. 2 to 10. FIG. 2 shows the photoacoustic detecting optical system in accordance with a first embodiment of the present invention in its block form. This optical system is composed of a modulated laser irradiation optical system 510 having a He-Ne infrared laser (wavelength: 1.2 $\mu$m) 31 for generating photoacoustic effect as a light source; a Michelson interferometer optical system 520 for detecting a photoacoustic signal; a laser irradiation optical system for auto-focusing 530; an auto-focusing optical system 540; and a signal processing system 550. In the modulated laser irradiation optical system 510, parallel light emitted from the He-Ne infrared laser 31 is intensity-modulated by an acoustic-electric modulation element 32 at a predetermined frequency. Its intermittent light is expanded to a beam having a desired diameter by a beam expander 33, which is thereafter focused by a lens 34 to its rear focal point 90 thereof. A pin-hole 35, which is provided at the focal point 90, shades the high order diffraction light components 101a and 101b around the peak part 100 of the focused beam spot as shown in FIG. 3. As a result, the light intensity distribution immediately after having passed the pin-hole 35 provides only the peak part 100 as shown in FIG. 4. Since the focal point 90 is also a front focal point of a lens 36, the light from the pin-hole 35, after having passed the lens 36, becomes a parallel light.

This parallel light, after having been reflected from a dichroic mirror 37 (light having a wavelength exceeding 1 $\mu$m is reflected and light having a wavelength of 1 $\mu$m or less penetrates), becomes a beam spot having the same light intensity distribution as shown in FIG. 4 again at a front focal point 91 of an objective lens 38, i.e. on a sample 42. Namely, the front focal point 90 of the lens 36 and the front focal point 91 of the lens 38 are in a conjugate relation and also in a confocal relation. A main feature of this embodiment resides in that by scanning a Z stage 41 on which the sample 42 is placed, as shown in FIG. 1, the front focal point 91 of the objective lens 38, i.e. the focused spot of the He-Ne infrared laser light is scanned inside the sample 42 in a depth direction thereof. The specifics of this therefor will be described later. A thermal distortion wave created at the focusing spot position 91 (front focal point of the objective lens 38) on the surface of or inside the sample generates an ultrasonic wave and also provide minute displacement on the surface of the sample 42.

In the Michelson interferometer optical system an Ar laser 31 (wavelength 0.515 $\mu$m) is expanded to a beam having a desired diameter by a beam expander 44, which is thereafter focused by a lens 45 to its rear focal point 92 thereof. A pin-hole 46, which is provided at the focal point 92, shades the high order diffraction light components around the peak part of the focused beam spot in the same manner as in FIG. 3. Since the focal point 92 is also a front focal point of a lens 49, the light from the pin-hole 46, after having passed the lens 49, becomes a parallel light.

This parallel light is separated into a P polarized light and an S polarized light. The P polarized light passes through a polarized light beam splitter 50. And further it passes a dichroic mirror 70 (the light having a wavelength exceeding 0.6 $\mu$m or less is passed and the light having a wavelength exceeding 0.6 $\mu$m is reflected), a beam splitter 71 (transmittance: reflectivity at the wavelength of 0.5~0.7 $\mu$m=7:3), a dichroic mirror 37 and $\lambda/4$ plate to become a circularly polarized light. Thus, this circularly polarized light is focused at the position of 91 on the sample 42 (front focal point of the objective lens 38) by the objective lens 38 to provide the same spot having light intensity distribution as shown in FIG. 4. The S polarized light is reflected from the polarized beam splitter 36 and passes $\lambda/4$ plate 51 to become a circularly polarized light which is incident to a reference mirror 52. The light reflected from the sample 42, which has the minute displacement generated on the sample surface as phase information, passes through the objective lens 38 and the $\lambda/4$ plate 55 to become the S polarized light which is reflected from the polarized light beam splitter 50. The light reflected from the reference mirror 52 passes through the $\lambda/4$ plate 51 to become the P polarized light which passed the polarized light beam splitter 50.

Figure 5:
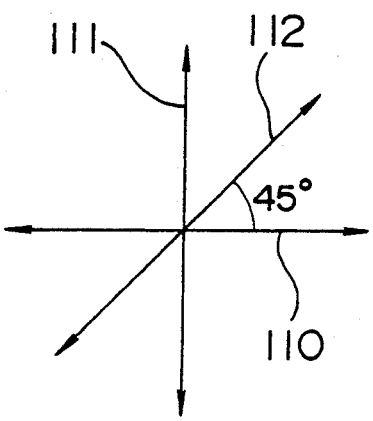
FIG. 5 is a view for explaining the polarization direction in a polarization plate.
Figure 6:
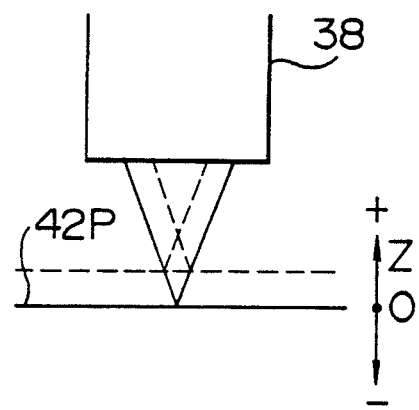
FIG. 6 is a view showing the elevation of a Z stage.
Figure 7:
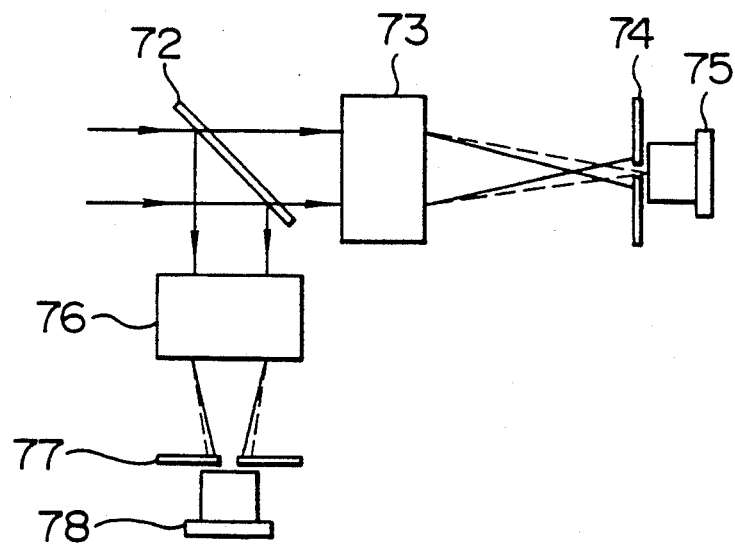
FIG. 7 is a view for explaining the operation of an auto-focusing optical system.

In FIG. 5, 110 represents the polarizing direction of the reflection light from the sample 42 and 111 represents that from the reference mirror 52. Since both reflection lights are orthogonal, they do not interfere with each other as they are. However, by inserting a polarization plate 56 into their optical path to place their polarization direction in a direction of 45 degrees as shown by 112 in FIG. 5, both reflection lights interfere with each other. The interference pattern thus formed, which includes the phase information relative to the minute displacement generated on the sample surface, is focused by a lens 57 at its rear focal point 93 and detected by a photoelectric converting element 63 such as a photodiode. Also, a pin-hole 62 is arranged at the rear focal point 93 in order to shade the stray light created in the objective lens 38, or noise light of the interference component created in a transparent film on the sample or the high order diffraction light component created due to the minute rugged sample surface.

As understood by the above description, in the Michelson interferometer optical system 520, the front focal point 92 of the lens 49, the front focal point 91 of the objective lens 38 and the rear focal point 93 of the lens 57 are in a conjugate relation and also in a confocal relation. The photoelectric-converted interference intensity signal is amplified by a preamplifier 64 and thereafter sent to a lock-in amplifier 81. The lock-in amplifier 81, using as a reference signal a modulated frequency signal from an oscillator 80 used for driving the acoustic-optical modulation element 32, extracts the modulated frequency component and phase component contained in the interference intensity signal. The frequency component and the phase component have information in a thermal diffusion area Vth defined by the frequency. Therefore, if there is a defect such as a crack inside this thermal diffusion area Vth the modulated frequency component in the interference intensity signal changes in its amplitude and phase so that the presence of the defect can be noticed.

As described previously, in this embodiment, by scanning the Z-stage 41 on which the sample 42 is mounted, as shown in FIG. 1, the front focal point 91 of the objective lens 38, i.e., the focusing spot of the He-Ne infrared laser light is scanned inside the sample 2 in the direction thereof. On the other hand, the focusing spot of the Ar laser light in the Michelson interferometer optical system 520 for detecting minute displacement on the surface of the sample 42 generated owing to the photoacoustic effect must be always focused on the surface of the sample 42 irrespectively of the position of the Z-stage 41. If not, the light reflected from the surface of the sample 42 is not completely focused at the position of the pin-hole 62 so that the amount of the light passing through the pin-hole 62 is largely reduced and the obtained interference intensity becomes very weak. As a result, it becomes difficult to provide information inside of the sample 42. However in this embodiment, by using this phenomenon conversely, an auto-focusing function with a very high accuracy can be added. This will be explained below.

The parallel light emitted from the He-Ne laser (wavelength 0.633 $\mu$m) 65 in the auto-focusing laser irradiation optical system 530 is expanded to a beam having a desired diameter by a beam expander 66, which is thereafter focused by a lens 67 to its rear focal point 94 thereof. A pin-hole 68, which is provided at the focal point 94, shades the high order diffraction light component around the peak part of the focused beam spot as shown in FIG. 3. The front focal point 91 of the objective lens 38 and the rear focal point 94 of the lens 67 are in a confocal relation. Since the focal point 94 is also a front focal point of a lens 69, the light from the pin-hole 68, after having passed the lens 69, becomes a parallel light.

This parallel light, after having been reflected from a dichroic mirror 70 and passed through a beam splitter 71 and a dichroic mirror 37, is focused on the position of 91 of the sample 42 (which corresponds to the front focal point of the objective lens 38) to provide a beam spot having the same light intensity distribution as shown in FIG. 4. The light reflected from the sample 42, after having passed through the objective lens 38 and the dichroic mirror 37, is reflected by the beam splitter 71 and is guided to the auto-focusing optical system 540. It is further separated into two beams by a beam splitter 72, which are focused by lenses 73 and 76 at their rear focal point. Arranged on the respective light paths are photoelectric converting elements (e.g. photodiodes) 75 and 78 and further arranged are pin-holes 74 and 77 immediately therebefore. In this case, the pin-hole 74 is located behind the rear focal point Fa of the lens 73 whereas the pin-hole 77 is located before the rear focal point Fb (=Fa) of the lens 77. For convenience of explanation, it is now assumed that the objective lens 38 is chromatic-aberration-corrected for the He-Ne infrared laser light (wavelength 1.2 $\mu$m) the He-Ne infrared laser light (wavelength 0.633 $\mu$m) and the Ar laser light (wavelength 0.515 $\mu$m), and each light beam is focused on the surface of the sample 42. The position of the Z stage at this time is used as a reference position. If the Z stage rises to shift the sample surface 42 toward its plus side (broken line in FIG. 6), as indicated by the broken line in FIG. 7, the light amount passing through the pin-hole 74 is increased whereas the light amount passing through pin-hole 77 is decreased.

Figure 8:
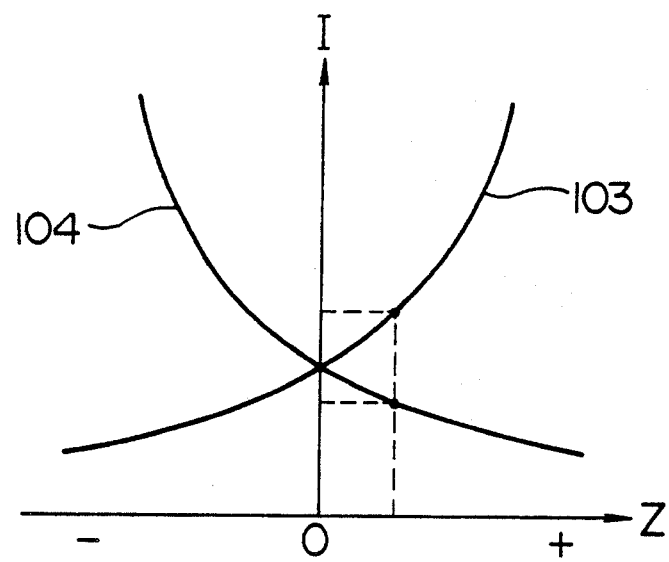
FIG. 8 is a graph showing the relation between the shifting amount of the Z stage and the output current a photoelectric converting element.
Figure 10:
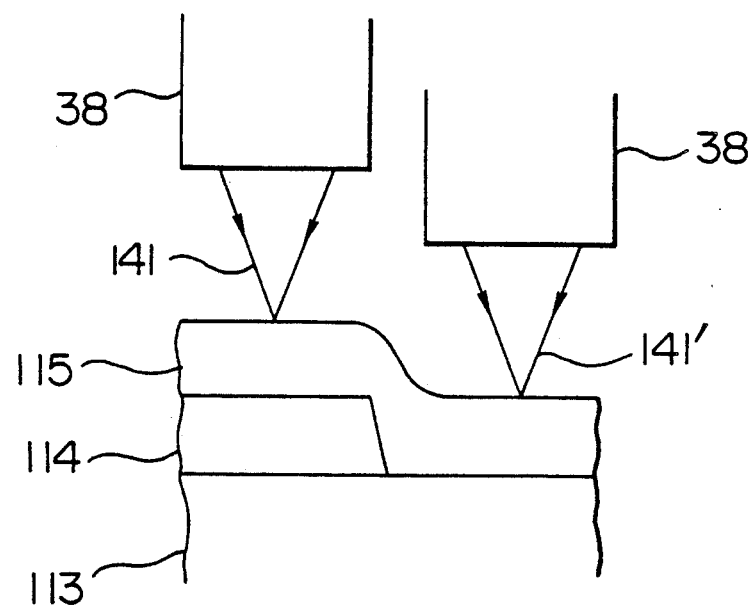
FIG. 10 is a view showing the manner of focusing the laser beam on the rugged surface of a sample.

FIG. 8 shows the relation between the shifting amount of Z stage and the respective output currents 103 and 104 from the photoelectric converting elements 75 and 78. By comparing both output currents in a comparator circuit 79 in FIG. 2, the position of Z stage 41 can be always monitored.

Figure 9A:
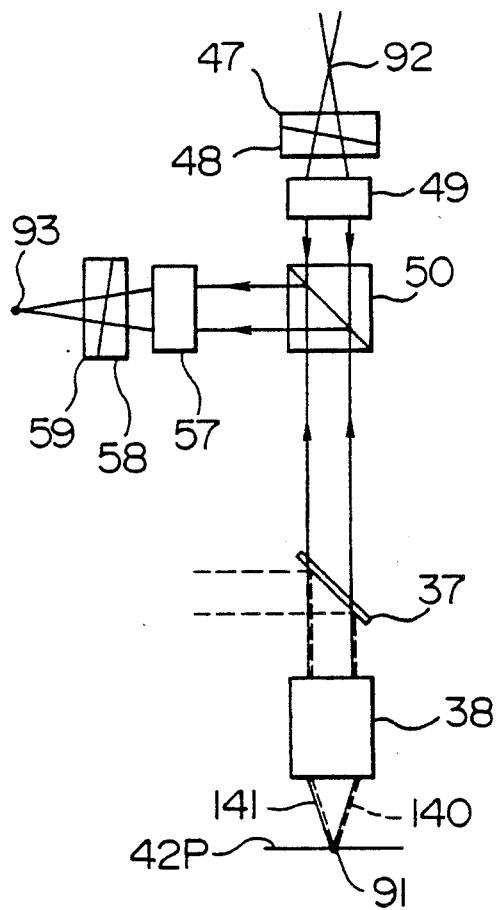
FIGS. 9A and 9B are views for explaining the method controlling the focusing position of a laser beam.
Figure 9B:
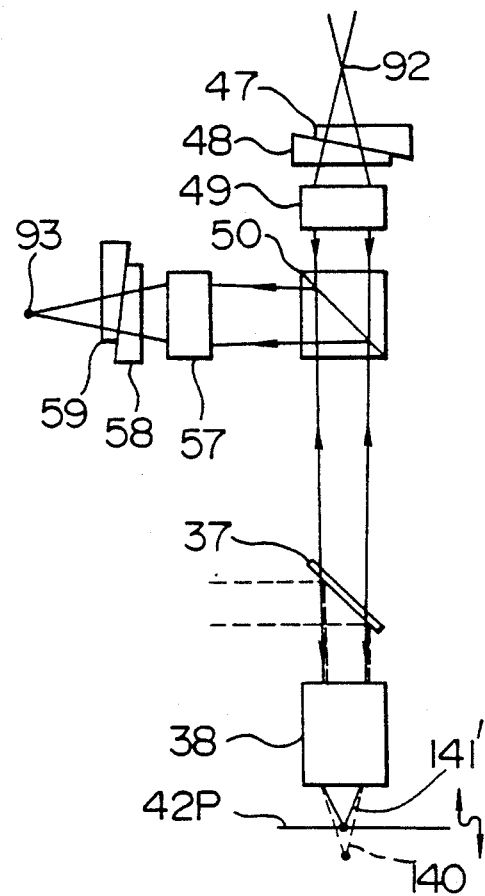

FIGS. 9A and 9B show methods for controlling, using the Z stage shifting signal from the comparator circuit 79 the focusing position of the beam from the Ar laser 43 in the Michelson interferometer optical system 520 and the focusing position of the beam reflected from the sample surface 42P. In FIG. 9A, both of the beam 140 (broken line) from the He-Ne infrared laser 31 which is excited light and the beam 141 (solid line) from the Ar laser 43 are focused at the position of 91 on the sample surface 42P. On the other hand, FIG. 9B shows the manner in which by elevating the Z stage 41, the focusing spot of the beam 140' from the He-Ne infrared laser 31 is scanned inside the sample in the depth direction thereof. When the Z stage 41 is elevated, the beam 141 from the Ar laser 43 will not be focused on the sample surface 42P. In order to obviate this, the comparator circuit 79 in the auto-focusing optical system 540 sends a Z stage shifting signal to a PZT (Piezoelectric-transducer) drive circuit 54 to drive a PZT device 53 so as to minutely shift a wedge-shaped glass 47 so that the beam 141' from the Ar laser is focused on the sample surface 42P. Likewise, another PZT element 61 is driven by another PZT drive circuit 60 so as to minutely shift another wedge-shaped glass 59 so that the light reflected from the sample surface 42P is focused at the position of 93 of the photo-electric converting element 63. By means of the above operation, irrespectively of the movement of the Z stage 41, the beam 141' from the Ar laser 43 can be always focused on the sample surface 42P and also the light reflected from the sample surface 42P can be on the photoelectric converting means 63.

Further, in the signal processing system 550, the shifting signal for the Z stage 41 and the XY stage, and the output signal from a lock-in amplifier 81 are processed by a computer 82. Accordingly, the three-dimensional photoacoustic image inside the sample 42 is displayed on a display (e.g. monitor television) 83. The circuit 79 supplies a signal of the beam spot position information (in the depth direction) to the computer 82 for the production of the displayed image.

In accordance with this embodiment, by using infrared light as excited light, it is possible to scan the focusing spot of the excited light in the depth direction inside the sample such as Si which is opaque to visible light. Thus, without reducing the resolutions in the transverse and depth directions of the sample, it is possible to stably detect the internal information (internal defect) of the sample (e.g. semiconductor device) at any depth position. Moreover, by constructing all the optical systems in a confocal optical system, the transverse resolution and detection sensitivity for a photoacoustic signal can be improved and also the influence from multi-interference in a multi-layer film can be reduced. Furthermore, by providing an auto-focusing optical system constructed in a confocal optical system to monitor the position of the beam spot on the sample surface and also vary the position of the laser focusing spot in the Michelson interferometer optical system it is possible to always form the focusing spot having a minimum size on the sample surface and on the photoelectric converting element, thereby stably detecting the photoacoustic signal. Further, by means of the above functions, even in the case of the sample having a rugged surface (e.g. semiconductor wafer in which a circuit pattern consisting of a silicon dioxide SiO₂ and aluminum 115 is formed in a silicon substrate, the laser light can be stably focused on the sample surface by adjusting the light incident on the sample surface.

Figure 11:
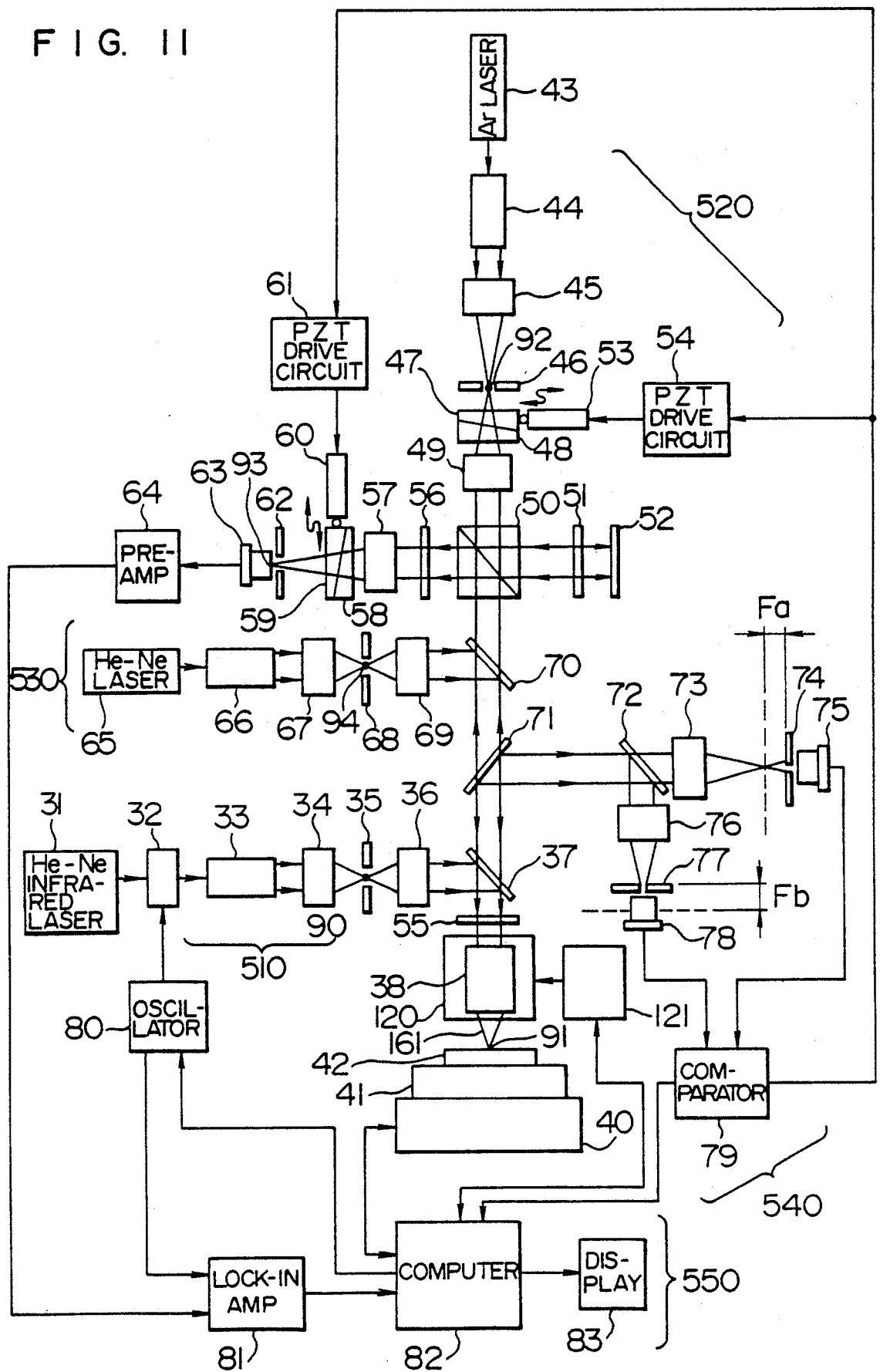
FIG. 11 is a block diagram showing the photoacoustic signal detecting optical system according to a second embodiment of the present invention.

Now referring to FIGS. 11 to 13, a second embodiment of the present invention will be explained. FIG. 11 shows the arrangement of a photoacoustic detection optical system in accordance with this embodiment. As in the first embodiment, this optical system is composed of a modulated laser irradiation optical system 510 having a He-Ne infrared laser (wavelength: 1.2 μm) 31 for generating photoacoustic effect as a light source; a Michelson interferometer optical system 520 for detecting a photoacoustic signal; a laser irradiation optical system for auto-focusing 530; an auto-focusing optical system 540; and a signal processing system 550. Since the construction and function of each optical system are entirely the same as those in the first embodiment, they are not explained here. This embodiment is different from the first embodiment in that in the first embodiment, the focusing spot of the He-Ne infrared laser light that is excited light is scanned inside the sample by shifting the Z stage whereas in this embodiment this function is implemented by minutely shifting an objective lens 38 in the direction of the optical axis thereof.

FIG. 12 shows the mechanism for minutely shifting the objective lens 38. As seen from FIG. 12, the objective lens 38 is fixed to a holder 130 which is held in another holder 120 through a plate springs 131a and 131b. In operation, a minute shift signal sent from a computer 82 drives a PZT element 133 through a PZT drive circuit 121 so as to minutely shift the objective lens 38 in the optical axis direction thereof.

Figure 13A:
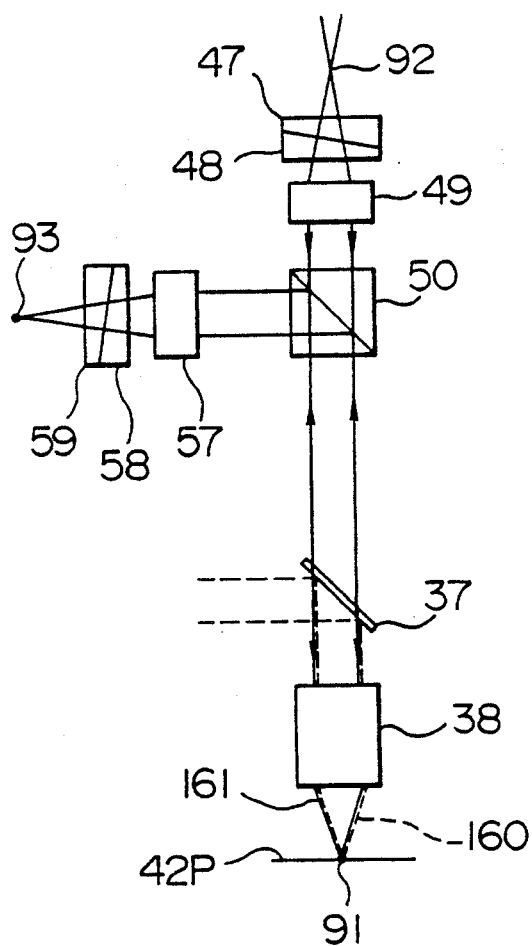
FIGS. 13A and 13B are views for explaining the method for controlling the focusing position of a laser beam.
Figure 13B:
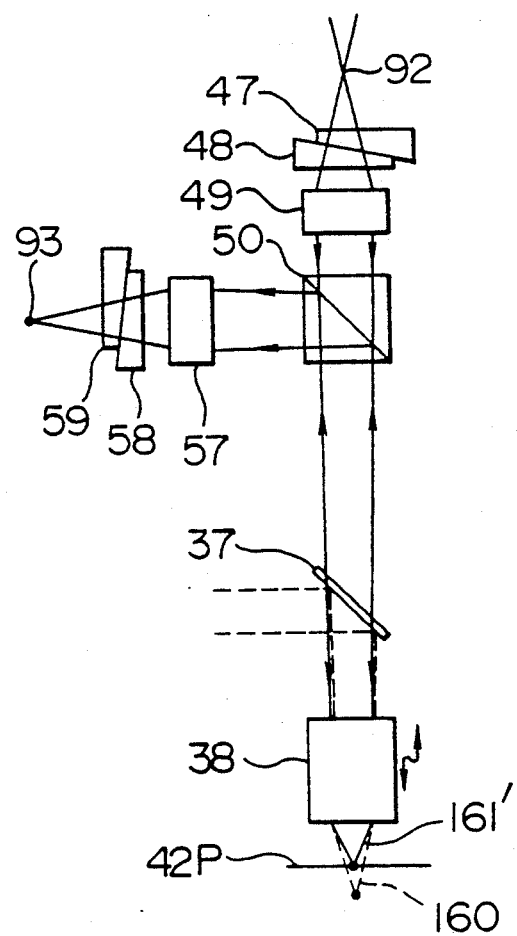

FIGS. 13A and 13B show methods for controlling, using the objective lens shifting signal from the comparator circuit 79 the focusing position of the beam from the Ar laser 43 in the Michelson interferometer optical system 520 and the focusing position of the beam reflected from the sample surface 42P. In FIG. 13A, both of the beam 160 (broken line) from the He-Ne infrared laser 31 which is excited light and the beam 161 (solid line) from the Ar laser 43 are focused at the position of 91 on the sample surface 42P. On the other hand, FIG. 13B shows the manner in which by lowering the objective lens 38, the focusing spot of the beam 160' from the He-Ne infrared laser 31 is scanned inside the sample in the depth direction thereof. In the same manner as in the first embodiment, the comparator circuit 79 in the auto-focusing optical system 540 sends an objective lens shifting signal to a PZT (Piezo-electric-transducer) drive circuit 54 to drive a PZT device 53 so as to minutely shift a wedge-shaped glass 54 so that the beam 161' from the Ar laser is focused on the sample surface 42P Likewise, another PZT element 61 is driven by another PZT drive circuit 60 so as to minutely shift another wedge-shaped glass 59 so that the light reflected from the sample surface 42P is focused to the position of 93 of the photoelectric converting element 63. By means of the above operation, irrespectively of the movement of the objective lens 38, the beam 141' from the Ar laser 43 can be always focused on the sample surface 42P and also the light reflected from the sample surface 42P can be focused on the photoelectric converting means 63.

Further, in the signal processing system 550, the shifting signal for the Z stage 41 and the XY stage, and the output signal from a lock-in amplifier 81 are processed by a computer 82. Accordingly, the three-dimensional photoacoustic image inside the sample 42 is displayed on a display (e.g. monitor television) 83.

In accordance with this embodiment, the same effect as the first embodiment can be obtained.

Figure 14:
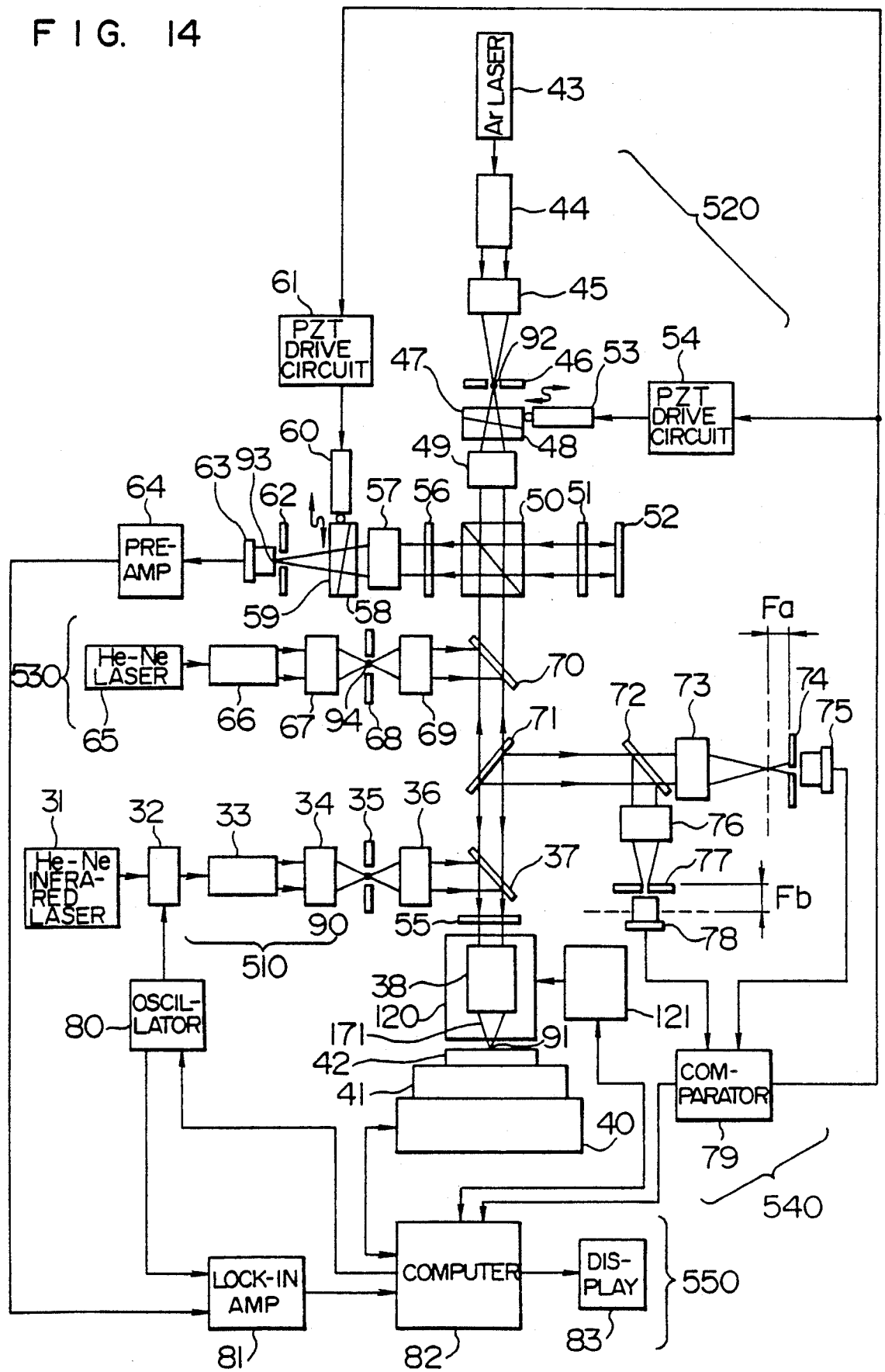
FIG. 14 is a block diagram showing the photoacoustic signal detecting optical system according to a third embodiment of the present invention.
Figure 15:
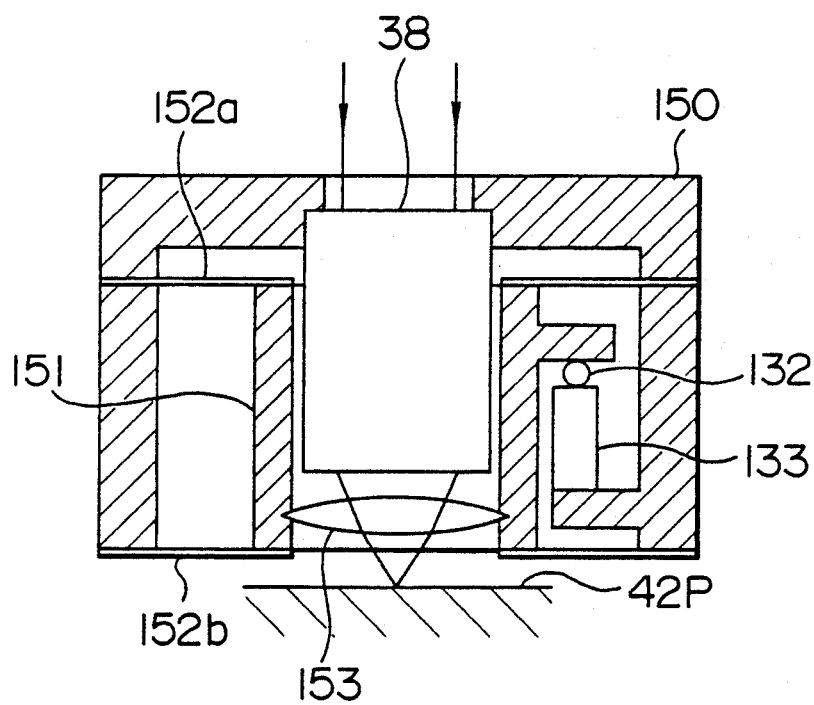
FIG. 15 is a sectional view for explaining the mechanism for minutely shifting a relay lens.

Now referring to FIGS. 14 to 17, a third embodiment will be explained. FIG. 14 shows the arrangement of a photoacoustic signal detection optical system according to this embodiment. Since the basic arrangement and function of this optical system is entirely the same as those in the first embodiment, they are not explained here. This embodiment is different from the first embodiment in that in this embodiment, as shown in FIG. 15, a relay lens 153 is inserted between the objective lens 38 and the sample 42; by minutely shifting the objective lens 38 in a direction of the optical axis thereof to effectively vary the focal length of the objective lens 38, the focusing beam spot from the He-Ne laser 31 that is excited light is scanned inside the sample. As seen from FIG. 15, the relay lens 151 is fixed to a holder 151 which is held in another holder 150 fixed to the objective lens 38 through a plate springs 152a and 152b. In operation, a minute shift signal sent from a computer 82 drives a PZT element 133 through a PZT drive circuit 121 so as to minutely shift the relay lens 151 in the optical axis direction thereof.

Figure 16:
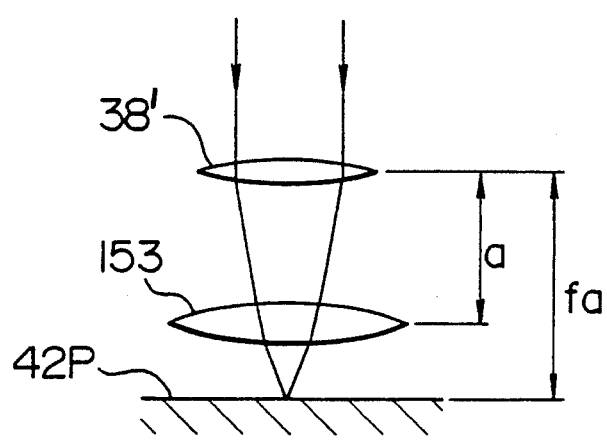
FIG. 16 is a view showing the arrangement of the objective lens and the relay lens.

FIG. 16 shows the arrangement of an objective lens 38' modeled as a single lens and the relay lens 153. Assuming that the focal length of the objective lens 38' is $f_o$, and the focal length of the relay lens is $f_r$, and the distance between both lenses is a, the distance from the objective lens 38' to the focusing position of laser beam spot, i.e. effective focal length $f_a$ can be expressed by $$f_a = \frac{f_o f_r + a(f_o - a)}{f_o + f_r - a} \qquad (2)$$

It can be understood that the effective focal length $f_a$ is increased with increase of the distance a.

Figure 17A:
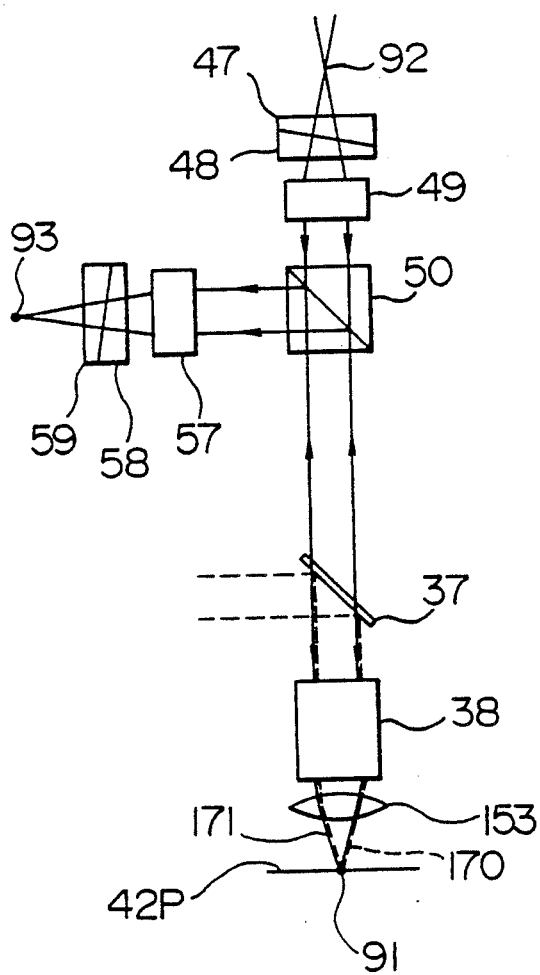
FIGS. 17A and 17B are views for explaining the method for controlling the focusing point of a laser beam.
Figure 17B:
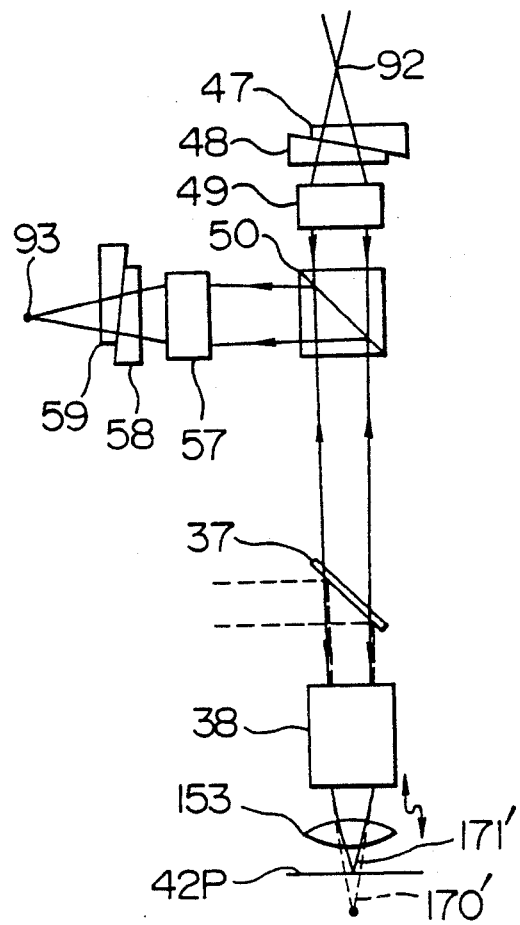

FIGS. 17A and 17B show methods for controlling, using the relay lens shifting signal from the comparator circuit 79 the focusing position of the beam from the Ar laser 43 in the Michelson interferometer optical system 520 and the focusing position of the beam reflected from the sample surface 42P. In FIG. 17A, both of the beam 170 (broken line) from the He-Ne infrared laser 31 which is excited light and the beam 1 (solid line) from the Ar laser 43 are focused at the position of 91 on the sample surface 42P. On the other hand, FIG. 17B shows the manner in which by lowering the relay lens 153, the focusing spot of the beam 170' from the He-Ne infrared laser 31 is scanned inside the sample in the depth direction thereof. By minutely wedge-shaped glasses 47 and 59 in the same manner as in the first and second embodiments, irrespectively of the movement of the relay lens 38, the beam 171' from the Ar laser 43 can be always focused on the sample surface 42P and also the light reflected from the sample surface 42P can be focused on the photoelectric converting means 63.

Further, in the signal processing system 550, the shifting signal for the Z stage 41 and the XY stage, and the output signal from a lock-in amplifier 81 are processed by a computer 82. Accordingly, the three-dimensional photoacoustic image inside the sample 42 is displayed on a display (e.g. monitor television) 83.

In accordance with this embodiment, the same effect as the first embodiment can be obtained Further, by adopting the technique of minutely shifting a single relay lens to move the focusing spot from the He-Ne infrared laser 31, the mechanical stability of the optical systems during operation can increased, the photoacoustic signal can be more stably detected.

Figure 18:
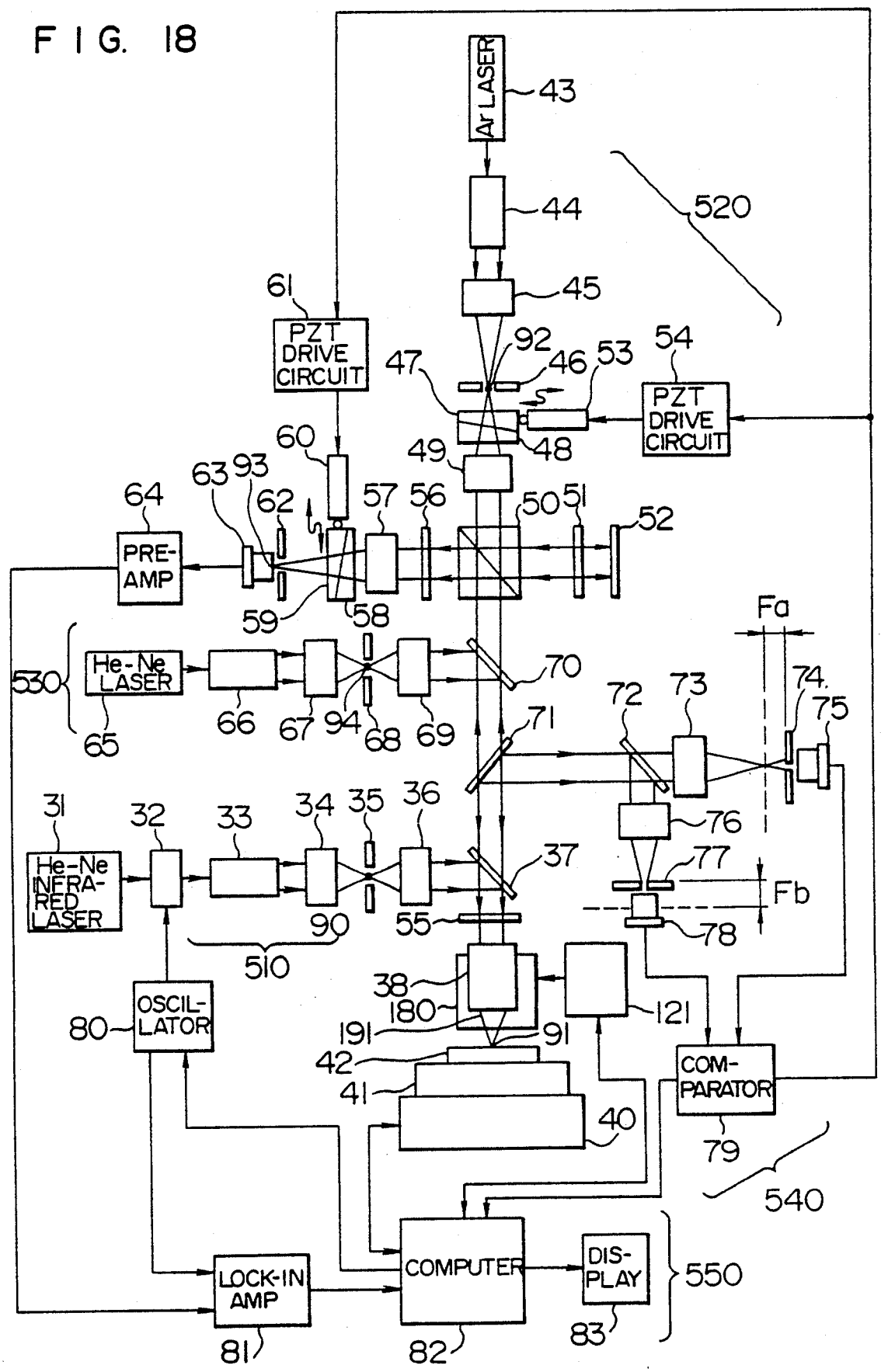
FIG. 18 is a block diagram showing the photoacoustic signal detecting optical system according to a fourth embodiment of the present invention.
Figure 19:
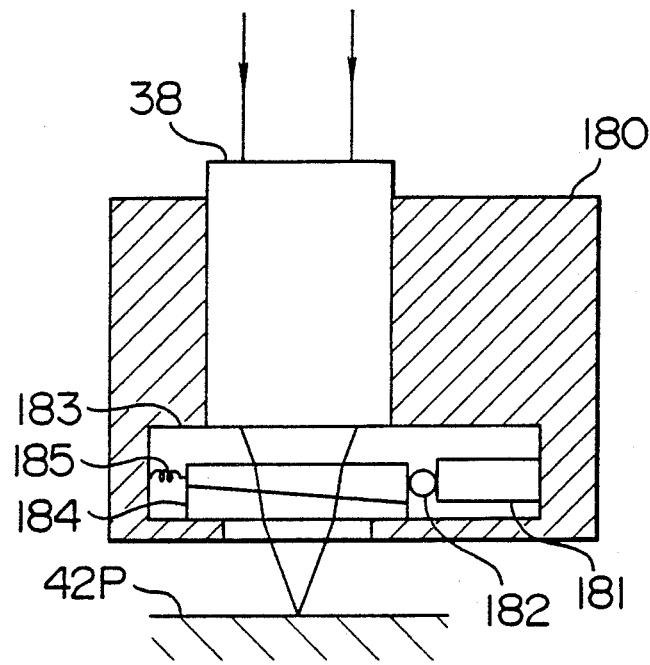
FIG. 19 is a sectional view for explaining the mechanism for minutely shifting a wedge-shaped glass.

Now referring to FIGS. 18 to 21, a fourth embodiment will be explained. FIG. 18 shows the arrangement of a photoacoustic signal detection optical system according to this embodiment. Since the basic arrangement and function of this optical system is entirely the same as those in the first embodiment, they are not explained here. This embodiment is different from the first embodiment in that in this embodiment, as shown in FIG. 19, a set of wedge-shaped glasses 183 and 184 are inserted between the objective lens 38 and the sample 42; by minutely shifting the wedge-shaped lens 183 in a direction perpendicular to the optical axis to effectively vary the focal length of the objective lens 38, the focusing beam spot from the He-Ne laser 31 that is excited light is scanned inside the sample. As seen from FIG. 19, the wedge-shaped glass 184 is fixed to a holder 180 together with the objective lens 38. In operation, a minute shift signal sent from the computer 82 drives a PZT element 181 through a PZT drive circuit so as to minutely shift the wedge-shaped glass 183 in the direction perpendicular to the optical axis.

Figure 20:
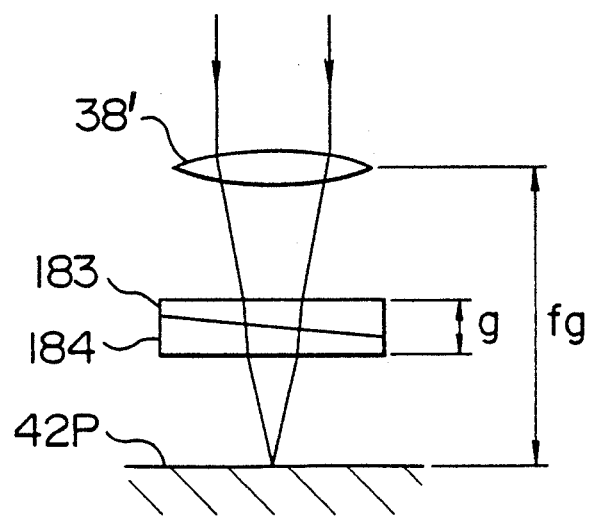
FIG. 20 is a view showing the arrangement of the objective lens and the wedge-shaped glass.
Figure 22:
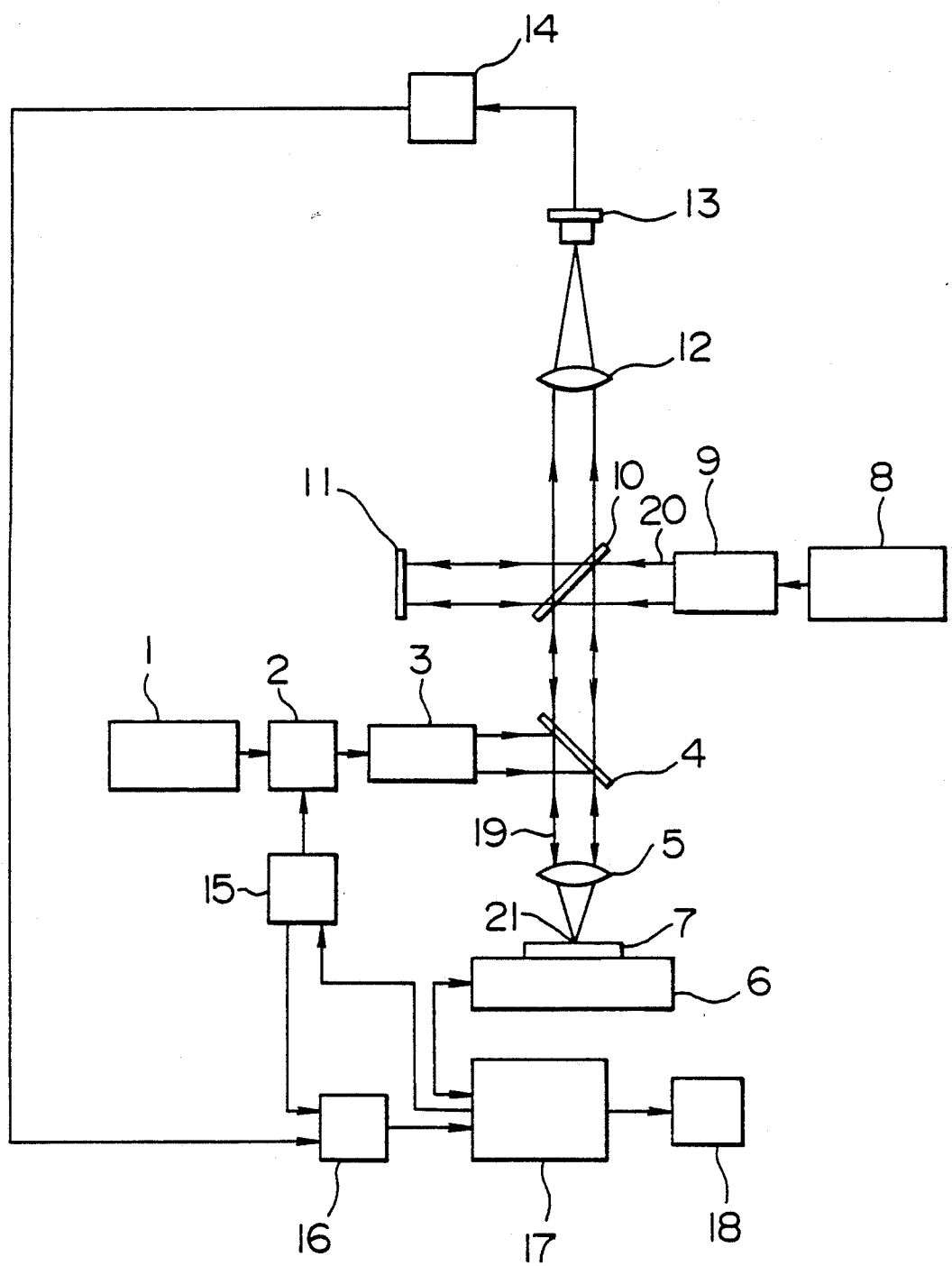
FIG. 22 is a block diagram showing the prior art photoacoustic signal detecting optical system.
Figure 23:
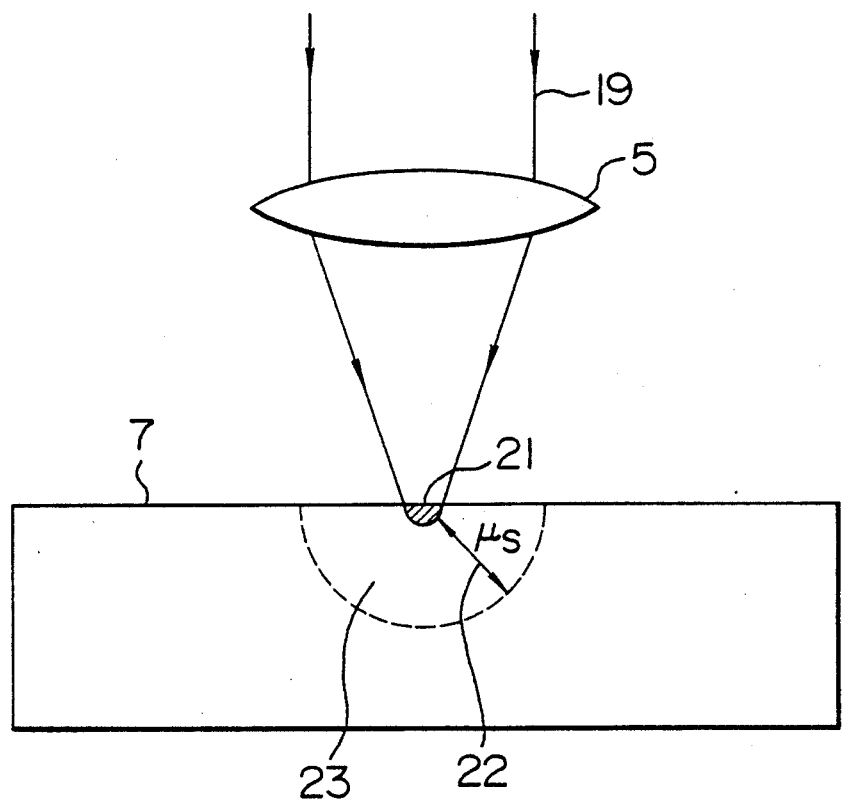
FIG. 23 is a view for explaining the theory of photoacoustic effect.

FIG. 20 shows the arrangement of the objective lens 38' modeled as a single lens and the wedge-shaped glasses 183 and 184. Now assuming that the focal length of the objective lens 38' is $f_o$, the sum of the thicknesses of the wedge-shaped glasses 183 and 184 is g, the refractive index of each wedge-shaped glass is $n_g$, and the refractive index of air is 1.0, the distance from the objective lens 38 to the focusing position of the laser beam spot, i.e. the effective focal length at the paraxial region can be expressed by $$f_g = \left(1 - \frac{1}{n_g}\right)g + f_o \quad (3)$$

It can be understood that the effective focal length $f_g$ is increased with increase of the sum of the thicknesses of the glasses.

FIGS. 21A and 21B show methods for controlling, using the wedge-shaped glass shifting signal from the comparator circuit 79 the focusing position of the beam from the Ar laser 43 in the Michelson interferometer optical system 520 and the focusing position of the beam reflected from the sample surface 42P. In FIG. 21A, both of the beam 170 (broken line) from the He-Ne infrared laser 31 which is excited light and the beam 171 (solid line) from the Ar laser 43 are focused at the position of 91 on the sample surface 42P. On the other hand, FIG. 21B shows the manner in which by minutely shifting the wedge-shaped glass 183 in the direction of increasing the thickness, the focusing spot of the beam 190' from the He-Ne infrared laser 31 is scanned inside the sample in the depth direction thereof. By minutely wedged-shaped glasses 47 and 59 in accordance with shifting amount of the beam spot in the same manner as in the first and second embodiments, irrespectively of the movement of the wedge-shaped glass 183, the beam 191' from the Ar laser 43 can be always focused on the sample surface 42P and also the light reflected from the sample surface 42P can be focused on the photoelectric converting means 63.

Further, in the signal processing system 550, the shifting signal for the Z stage 41 and the XY stage, and the output signal from a lock-in amplifier 82 are processed by a computer 82. Accordingly, the three-dimensional photoacoustic image inside the sample 42 is displayed on a display (e.g. monitor television) 83.

In accordance with this embodiment, the same effect as the first embodiment can be obtained. Further, by adopting the technique of minutely shifting a single relay lens to move the focusing spot from the He-Ne infrared laser 31, the mechanical stability of the optical systems during operation can be increased, the photoacoustic signal can be more stably detected In the four embodiments explained hitherto, the light from the He-Ne infrared laser (wavelength: 1.2 μm) is used. But if an infrared semiconductor laser is used, an injected current can be amplitude-modulated to provide an intensity-modulated beam. In this case, no photoacoustic modulation device is required Further, in the present invention, the excited light should not be limited to infrared light, but may be any light having a wavelength able penetrate a sample (e.g. semiconductor device).

Moreover, the means for detecting the minute displacement in the sample surface due to an ultrasonic wave generated in the sample should not be limited to a Michelson interferometer, but Mach-Zehender interferometer, a heterodyne interferometer, a PZT element, a microphone, etc. may be used.

We claim:

1. A method for detecting internal structure information of a sample comprising the steps of:
    generating a laser beam having a wavelength such that the laser beam penetrates through the sample;
    intensity-modulating said laser beam at a desired frequency for causing a short thermal diffusion length μs corresponding to a desired high resolution, said intensity-modulated laser beam being emitted from a first light source;
    focusing said intensity-modulated laser beam into a fine spot in a predetermined depth of the sample by removing high order diffraction light components; and
    detecting a thermal distortion due to a photoacoustic effect generated at a fine area in the sample by the focused fine spot of said intensity-modulated laser beam in said predetermined depth of the sample, by a thermal distortion detecting means,
    whereby said internal structure information of the sample is detected at said desired high resolution in accordance with a thermal distortion signal detected by said thermal distortion detecting means.

2. The method according to claim 1, wherein the step of detecting said thermal distortion includes detecting an interference light between a reference light and a light reflected from a surface above said fine area by controlling a focusing position of the light irradiated from a second light source on the surface so that the light is focused on the surface as the focused fine spot.

3. A method for detecting internal structure information of a semiconductor device comprising the steps of:
    generating a laser beam having a wavelength such that the laser beam penetrates through the semiconductor device;

intensity-modulating said laser beam at a desired frequency for causing a short thermal diffusion length μs corresponding to a desired high resolution, said intensity-modulated laser beam being emitted form a first light source;

focusing said intensity-modulated laser beam into a fine spot in a predetermined depth of the semiconductor device by removing high order diffraction light components; and detecting a thermal distortion due to a photoacoustic effect generated at a fine area in the semiconductor device by the focused fine spot of said intensity-modulated laser beam in said predetermined depth of the semiconductor device, by a thermal distortion detecting means, whereby said internal structure information of the semiconductor device is detected at said desired high resolution in accordance with a thermal distortion signal detected by said thermal distortion detecting means.

4. The method according to claim 3, wherein the step of detecting said thermal distortion includes detecting an interference light between a reference light and a light reflected from a surface above said fine area by controlling a focusing position of the light irradiated from a second light source on the surface so that the light is focused on the surface as the focused fine spot.

5. An apparatus for detecting internal structure information of a sample comprising:

a first light source for emitting a light beam having a wavelength which penetrates through the sample;

modulating means for intensity-modulating said light at a desired frequency for causing a short thermal diffusion length μs corresponding to a desired high resolution of the structure information;

focusing means for focusing said intensity-modulated light into a fine spot in a predetermined depth of the sample by removing high order diffraction light components; and thermal distortion detecting means for detecting thermal distortion due to a photoacoustic effect generated at a fine area in the sample by the focused fine spot of said intensity-modulated light, whereby the internal structure information of the sample is detected at said desired high resolution in accordance with said thermal distortion signal detected by said thermal distortion detecting means.

6. The apparatus according to claim 5, wherein said thermal distortion detecting means comprises focusing position control means for controlling a focusing position of light irradiated from a second light source on a sample surface above said fine area so that the irradiated light is focused on the sample surface as a fine spot, and interferometry detecting means for detecting light interference between a reference light and a light reflected from said sample surface.

7. The apparatus according to claim 5, further comprises light spot scanning means for minutely moving relatively the transmitted fine spot of said intensity-modulated light in the depth direction of the sample and depth detecting means for detecting the predetermined depth of the transmitted fine spot focused by said focusing means.

8. The apparatus according to claim 7, wherein said depth detecting means is formed by auto-focusing optical means for detecting light reflected from the sample surface above said fine area by a photodetector so as to generate a signal indicative of said predetermined depth.

9. The apparatus according to claim 5, wherein the light emitted from said first light source is infrared light.

10. The apparatus according to claim 6, wherein said focusing means includes an objective lens, and said interformetry detecting means is constructed in a confocal optical system.

11. The apparatus according to claim 10, wherein said focusing position control means comprises:

auto-focusing optical means for detecting the light reflected when light from a third light source is incident on the sample surface, thereby generating a signal indicative of the depth of the focused fine spot of said intensity-modulated light;

first adjusting means for adjusting the light emitted from said second light source in response to said spot depth indicating signal to always provide the light spot with a minimum size on said sample surface; and second adjusting means for adjusting the interference light reflected from said sample surface in response to said spot depth indicating signal to the light spot with a minimum size on said photoelectric converting element.

12. The apparatus according to claim 11, wherein said auto-focusing optical means comprises first and second photoelectric converting means for separating the light reflected from the sample surface when the light from said third light source is incident on the sample surface into first and second beams to differentially detect them.

13. The apparatus according to claim 12, wherein said first photoelectric converting means comprises, in order to detect said first beam, a first lens and a first pin-hole arranged behind its rear focal point; said second photoelectric converting means comprises, in order to detect said second beam, a second lens and a second pin-hole arranged before its front focal point; and each of said first and second adjusting means comprises a wedge-shaped glass and means for driving said glass in response to said spot depth indicating signal.

14. The apparatus according to claim 11, wherein said interferometry detecting means comprises:

beam splitter means for separating the light emitted from said second light source into first P polarized light and second S polarized light;

a first λ/4 plate for causing said first S polarized light to be incident on the sample surface as circularly-polarized light and returning the light reflected therefrom to said beam splitter means as second S polarized light;

a second λ/4 plate for causing said first S polarized light to be incident on a reference mirror as circularly-polarized light and returning the light reflected therefrom to said beam splitter means as second S polarized light; and polarization plate means for unifying the polarization directions of said second P polarized light and said S polarized light and sending them to said photoelectric converting means as light beams for interference.

15. The apparatus according to claim 11, wherein each of said focusing means, said interferometry detecting means, and said focusing position control means comprises means for shading a high order diffraction light component around the peak position of he focusing light spot.

16. The apparatus according to claim 7, wherein said light spot scanning means comprises means for selectively shifting said sample in a direction of the optical axis of said focusing means and in the direction perpendicular thereto.

17. The apparatus according to claim 7, wherein said light spot scanning means comprises a mechanism for minutely shifting said objective lens.

18. The apparatus according to claim 7, wherein said light spot scanning means comprises a mechanism for minutely shifting a relay lens provided between said objective lens and said sample.

19. The apparatus according to claim 7, wherein said light spot scanning means comprises a mechanism for minutely shifting a wedge-shaped glass provided between said objective lens and said sample.

* * * * *